United States Patent [19]

Asato et al.

[11] Patent Number: 4,614,746
[45] Date of Patent: Sep. 30, 1986

[54] 5-FLUOROBENZONITRILE DERIVATIVES FOR INCREASING THE LEAN MEAT TO FAT RATIO AND/OR ENHANCING THE GROWTH RATE OF WARM-BLOODED ANIMALS

[75] Inventors: Goro Asato, Titusville; Terence J. Bentley, East Windsor, both of N.J.

[73] Assignee: American Cyanamid Company, Stamford, Conn.

[21] Appl. No.: 714,240

[22] Filed: Mar. 21, 1985

[51] Int. Cl.$^4$ .................... A01N 37/34; C07C 121/80
[52] U.S. Cl. ...................................... 514/524; 558/422
[58] Field of Search ................... 260/465 E; 514/524; 558/422

[56] References Cited

U.S. PATENT DOCUMENTS 4,404,222  9/1983  Baker et al. .................... 424/304
4,407,819 10/1983  Kiernan et al. ................. 514/524
4,432,995  2/1984  Kiernan et al. ................. 424/304

FOREIGN PATENT DOCUMENTS 103830  9/1983  European Pat. Off. .

Primary Examiner—Dolph H. Torrence
Attorney, Agent, or Firm—Alice C. Brennan

[57] ABSTRACT

There are provided novel 5-fluorobenzonitrile derivatives which exhibit low $\beta_1$ heart stimulant activity and are useful for increasing the lean meat to fat ratio and/or enhancing the growth rate of warm-blooded animals by, orally or parenterally, administering to said animals an amount of a 5-fluorobenzonitrile derivative or a pharmacologically acceptable salt thereof effective for achieving one or more of the above-identified metabolic improvements in said warm-blooded animals.

13 Claims, No Drawings

5-FLUOROBENZONITRILE DERIVATIVES FOR INCREASING THE LEAN MEAT TO FAT RATIO AND/OR ENHANCING THE GROWTH RATE OF WARM-BLOODED ANIMALS

BACKGROUND OF THE INVENTION

Substitution products of 1-(amino-dihalophenyl)-2-aminoethanes and acid addition salts thereof were disclosed in U.S. Pat. No. 3,536,712, issued Oct. 27, 1970, as useful agents for enhancing blood circulation, and as bronchodilators, analgesics, antipyretics, antiphlogistics, and antitussives in warm-blooded animals. U.S. Pat. No. 3,574,211, then issued on Apr. 6, 1971, disclosed 1-(amino-monohalophenyl)-2-amino-alkanols and salts thereof as analgesics for warm-blooded animals and U.S. Pat. No. 4,119,710, issued Oct. 10, 1978, described a variety of 1-(p-aminophenyl)-2-aminoethanols and salts as utero-spasmolytics, bronchospasmolytics, analgesics and antispastics for the skeletal musculature. These compounds were also said to be especially active as $\beta_2$-receptor mimetics and $\beta_1$-receptor blockers.

Other related 1-(amino-dihalophenyl)-2-aminoethanols and their derivatives were disclosed in Japanese Kokai No. 77 83,619 (Chemical Abstracts, 87,201061r), German Offenlegungsschrift No. 2,804,625 (1979), German Offenlegungsschrift No. 2,157,040 (1973), German Offenlegungsschrift No. 2,261,914 (1974), European patent application No. 8,715 (1980), Netherlands patent application No. 7,303,612 (1973). These applications disclosed uses selected from analgesics, broncholytic, antiinflammatory, uterine spasmolytic, $\beta$-mimetic and/or $\beta$-blocking activities, antispasmolytic activity on cross-striped muscle structure, for tocology, reducing blood pressure by peripheral vasodilation and mobilizing body fat, and for treating allergies.

J. A. Kiernan and P. K. Baker, U.S. Pat. Nos. 4,404,222 and 4,407,819, surprisingly discovered that many of the phenylethanolamine derivatives described in the above-mentioned patents, patent applications, and/or references were highly effective as antilipogenic agents and/or growth promoters for meat-producing animals when orally or parenterally administered thereto on a daily basis at very low dosages. More surprisingly, the patentees' also found that administration of the above-said phenylethanolamine derivatives to meat-producing animals, as indicated above, markedly increased the lean meat to fat ratio of said animals.

These discoveries of J. A. Kiernan and P. K. Baker provide many advantages. For poultrymen, swine raisers, and cattle and sheep ranchers, the Kiernan and Baker invention translates into larger, leaner animals that command higher prices for improved carcass weight and quality. For pet owners and veterinarians, said invention provides a means for easily and effectively trimming excess fat from pet animals thereby producing a leaner, more vibrant pet.

Recently, Offenlegungsschrift DE No. 3,306,159 A1 (European Patent Application 103830) was published describing substituted phenylethylamine derivatives which were said to be growth promoters for pigs, cows, poultry, cats, dogs, rabbits, fur animals, fish, and reptiles.

Although it is apparent from the patents, patent applications, and papers referred to above, that phenylethane and phenylethanolamine derivatives and salts have been synthesized and evaluated for a variety of uses; the compounds of the invention in the subject Application are not specifically disclosed.

SUMMARY OF THE INVENTION

The novel compounds of this invention are depicted by formula I below:

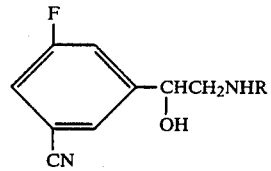

wherein R is isopropyl or tert-butyl; and the optical isomers thereof and the non-toxic, pharmacologically acceptable acid addition salts thereof.

In contrast to the prior art compounds described above, the compounds of the present invention are highly effective for increasing the deposition of lean meat, i.e., muscle or protein, in meat-producing animals and for increasing the lean meat to fat ratio in said animals. Advantageously, the compounds of this invention are also effective for increasing the growth rate of said meat-producing animals and have been found to have the very important advantage that they exhibit very low $\beta_1$ heart stimulant activity as compared to the most effective art compounds that are effective for increasing deposition of lean meat, increasing the lean meat to fat ratio, and/or increasing the growth rate of meat-producing animals and domestic pets.

The compounds of the invention exhibit surprisingly low $\beta_1$ heart stimulant activity. As such, they impart a significantly improved or added margin of safety in their use over art compounds that exhibit substantial $\beta_1$ heart stimulant activity.

DESCRIPTION OF THE PREFERRED EMBODIMENTS

The compounds of the present invention can be prepared by reacting 2-amino-5-fluoroacetophenone with N-bromosuccinimide. The reaction is preferably conducted at a temperature between about 0° C. and 35° C., under a blanket of inert gas such as nitrogen, in the presence of an aprotic solvent such as methylene dichloride, chloroform, ethylene chloride, or chlorobenzene to yield 2-amino-3-bromo-5-fluoroacetophenone.

The thus-formed 2-amino-3-bromo-5-fluoroacetophenone is then deaminated by reaction thereof with sodium nitrite in the presence of acid, preferably a 1:1 mixture of hypophosphorous acid and acetic acid. The reaction yields 3-bromo-5-fluoroacetophenone which is then converted to 3-cyano-5-fluoroacetophenone by reaction with cuprous cyanide. The reaction is preferably carried out by heating the above-said reactants to reflux temperature in the presence of an inert organic solvent, such as dimethylformamide or N-methylpyrrolidone, for several hours.

The thus-prepared 3-cyano-5-fluoroacetophenone is then dispersed in a chlorinated hydrocarbon solvent, such as dichloromethane, chloroform, or ethylene dichloride, containing a catalytic amount of hydrobromic acid in acetic acid. The mixture is heated to reflux temperature and treated with bromine to yield 3-cyano-5-fluorophenacyl bromide.

The 3-cyano-5-fluorophenacyl bromide from the above reaction is then dispersed in alcohol, preferably methanol, and reduced with sodium borohydride or sodium cyanoborohydride, or other reducing agents, such as hydrogen and a catalyst, e.g., platinum, palladium, or the like. The reaction yields 3-(2-bromo-1-hydroxyethyl)-5-fluorobenzonitrile which is readily converted to the formula I, 3-[2-(tert-butylamino)-1-hydroxyethyl]-5-fluorobenzonitrile or the 3-fluoro-5-[1-hydroxy-2-(isopropylamino)ethyl]-benzonitrile by reaction with t-butylamine or isopropylamine in the presence of ethanol.

Use of other amines which may be represented by the structure $NHR_1R_2$, wherein $R_1$ and $R_2$ each represent H, $C_1$–$C_6$ alkyl or $C_3$–$C_6$ cycloalkyl, will, of course, yield the corresponding 5-fluorobenzonitrites similar to formula I but having an $NR_1R_2$ function substituted for the formula I NHR functionality.

The above reactions are illustrated in Flow Diagram I below.

FLOW DIAGRAM I
PERPARATION OF FORMULA I
5-FLUOROBENZONITRILES

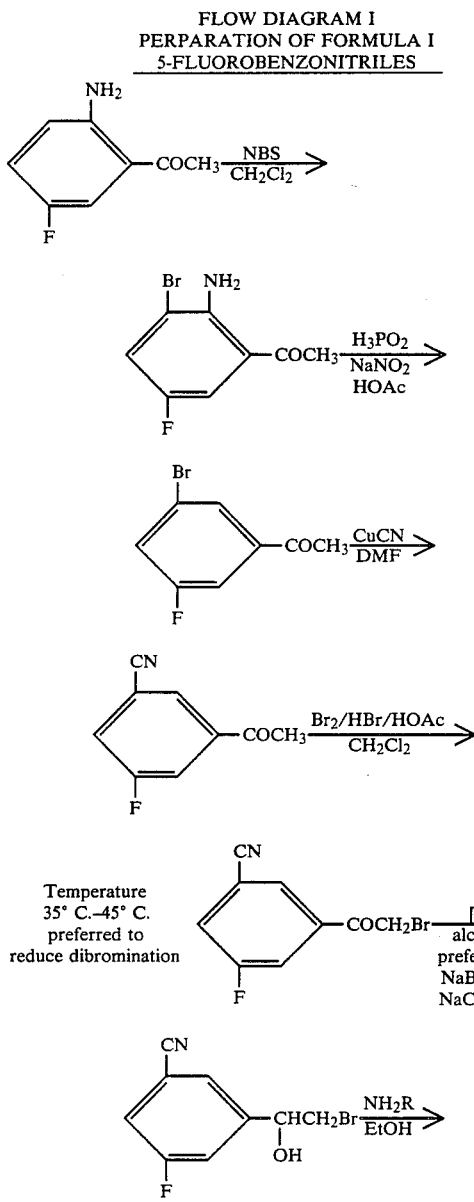

-continued
FLOW DIAGRAM I
PERPARATION OF FORMULA I
5-FLUOROBENZONITRILES

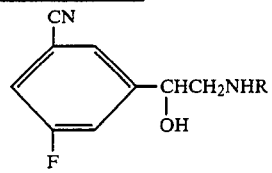

Formula I

Compounds of formula I, having the structural formula

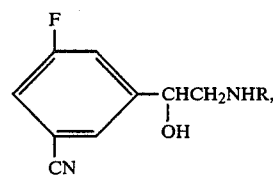

are unique in that they exhibit low $\beta_1$ heart stimulant activity and are highly effective for improving the lean meat to fat ratio in meat-producing animals and as antilipogenic agents therefore. These compounds are also useful as intermediates for the preparation of other novel animal growth-promoting compounds and antilipogenic agents. These latter compounds are depicted by formulas II and III illustrated below.

Formula II has the structure:

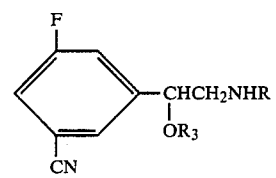

wherein R is isopropyl or t-butyl; and $R_3$ is $C_1$–$C_6$ alkyl, benzyl, phenyl or allyl; and includes the optical isomers thereof and the pharmocologically acceptable salts thereof. Formula III has the structure:

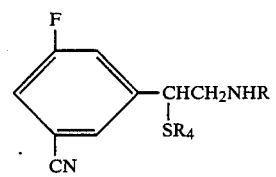

wherein R is isopropyl or t-butyl; $R_4$ is hydrogen, $C_1$–$C_6$ alkyl, benzyl, phenyl or allyl; and includes the optical isomers thereof and the pharmacologically acceptable salts thereof.

Formula II compounds, wherein R and $R_3$ are as described above, can be prepared from the formula I alcohol by treating said-formula I alcohol with thionyl chloride under a blanket of inert gas, preferably nitrogen, at a temperature of from about 0° C. to 10° C. This reaction yields the halo compound which can be isolated by conventional methods. The thus-obtained halo compound is then reacted with an appropriate alcohol or mercaptan under a blanket of inert gas, such as nitrogen, at a temperature between 0° C. and 50° C., to yield, respectively, the formula II alcohol or the formula III mercaptan. The reactions are graphically illustrated below (Scheme 1).

Scheme 1

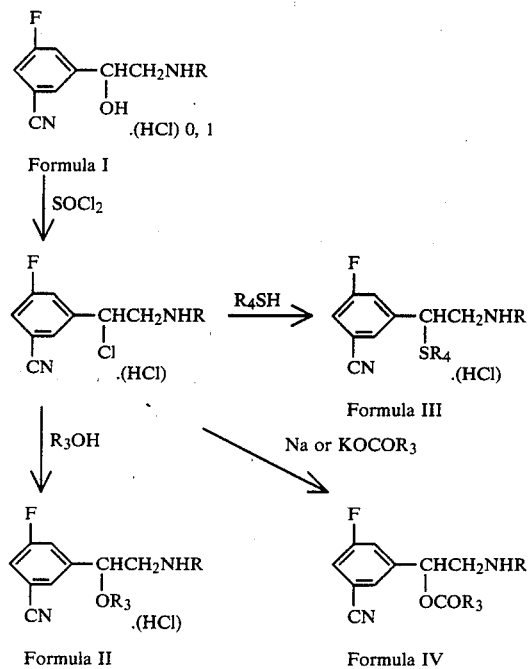

The formula I 5-fluorobenzonitriles can also be used as intermediates for the preparation of novel formula IV alkanoyl and aroyl 5-fluorobenzonitriles which are animal growth promoters and antilipogenic agents particularly useful for the treatment of meat-producing animals. The formula IV compounds have the structure:

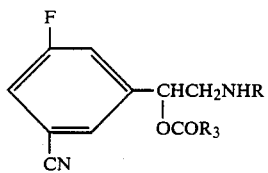

wherein R is isopropyl or t-butyl; $R_3$ is $C_1$–$C_6$ alkyl, benzyl, phenyl or allyl; and include the optical isomers thereof and the pharmacologically acceptable salts thereof.

These formula IV compounds are prepared by reacting the formula I 5-fluorobenzonitrile with an equivalent or slight excess of an acid anhydride represented by the structure: $(R_3CO-)_2O$ wherein $R_3$ is as described above. The reaction is conducted in the presence of an inert solvent such as a chlorinated hydrocarbon or an aromatic solvent at a temperature between about 0° C. and 25° C. with or without an organic base such as a tertiary amine or pyridine. The reaction may be graphically illustrated as follows:

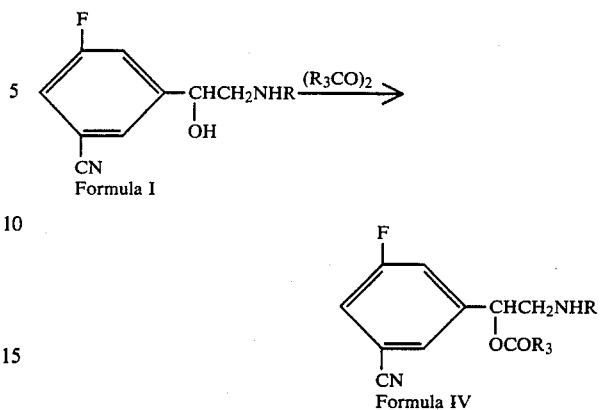

Another method for preparing formula IV compounds is to react the chloro intermediate described in Scheme 1 with a sodium or potassium salt of $R_3COOH$ in an inert solvent such as 1,2-dimethoxyethane, tetrahydrofuran, or 2-methoxyethyl ether at 25° C. to 60° C. until the reaction is completed.

Another type of novel growth-promoting and antilipogenic compound that can be prepared from formula I compounds is a formula IV compound as follows:

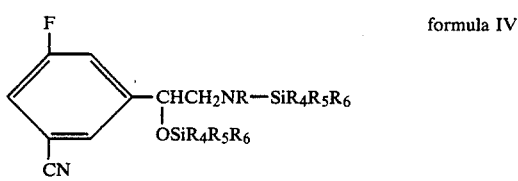

wherein $R_4$, $R_5$, $R_6$ are straight- or branched-chain alkyl $C_1$–$C_6$, which may be the same or different alkyl chains for each of these $R_4$–$R_6$ groups.

These compounds are prepared by reacting formula I compounds with a silicon compound of the formula $R_4R_5R_6SiX$, wherein X is halogen, $OSO_2CF_3$, $OSiR_4R_5R_6$ or $OSO_2OSiR_4R_5R_6$.

The 5-fluorobenzonitrile derivatives of this invention, which are represented by formula I, can be administered either orally or parenterally to domestic or farm animals with resultant increases in growth rates and/or enhancement of the lean meat to fat ratio in these animals. The active compounds may be mixed directly with animal feeds or, preferably, prepared in the form of an animal-feed premix, animal-feed concentrate, or feed supplement which can be blended with the feed or applied as a top dressing thereto. Regardless of which procedure is selected for administration, the active compound should be proffered in an amount sufficient to provide from about 0.05 to 200 ppm of active compound or preferably 0.05 to 100 ppm of active compound in the total feed.

Animal-feed premixes, supplements or concentrates are readily prepared by mixing, on a weight basis, about 0.5 to 50% of a 5-fluorobenzonitrile derivative or a pharmacologically acceptable salt thereof with about 50 to 99.5% of an edible diluent. Diluents suitable for use in the manufacture of animal-feed supplements, concentrates, and premixes include: corn meal, soybean meal, bone meal, alfalfa meal, cottonseed oil meal, urea, molasses, and other similar materials. Use of the diluents in feed supplements, concentrates, and premixes improves uniformity of distribution of the active ingredient in the finished feed.

Feeds for swine, cattle, sheep, and goats generally contain about 0.05 to 200 grams of active ingredient per ton of feed with an optimum level of about 0.125 to 100 grams of active ingredient per ton of feed. Poultry and domestic-pet feeds are usually prepared in such a manner as to contain from about 0.05 to 100 grams and most preferably about 0.1 to 100 grams of active ingredient per ton of feed.

For parenteral administration of the active ingredient, the formula I 5-fluorobenzonitrile or pharmacologically acceptable salt thereof, is formulated as a paste or pellet and administered to the animals by subcutaneous injection. This procedure involves injection of a sufficient amount of the formulated paste or a sufficient number of pellets which contain the formula I compound to provide the animals with about 0.001 to 100 mg/kg of body weight/day of said active compound. The preferred dosage for swine, cattle, sheep, and goats ranges from about 0.001 to 50 mg/day/kg of body weight of the 5-fluorobenzonitrile or pharmacologically acceptable salt thereof. The preferred dosage of the formula I compound for poultry and domestic pets ranges from about 0.001 to 10 mg/day/kg of animal body weight.

Paste or gel formulations suitable for subcutaneous injection can be prepared by dispersing a formula I 5-fluorobenzonitrile or pharmacologically acceptable salt thereof in a pharmcologically acceptable diluent, such as butylene glycol, peanut oil, corn oil, seasame oil, or a clear aqueous, thermally reversible, gel composition.

A typical gel formulation can be prepared in accordance with the following procedure.

The gellant phase is prepared by slurring the gellant 15% to 50% and preferably 15% to 35% by weight of formulation in propylene glycol 14% to 30% by weight for 15 minutes to one hour under reduced pressure 25 to 50 mm Hg at room temperature. The gellant selected is a nonionic surfactant of structure α-hydro-ω-hydroxy-poly(oxyethylene)poly(oxypropylene)poly(oxyethylene) block copolymer, average molecular weight 12,500; mp 56° C.; Brookfield viscosity of 3,100 at 77° C.; surface tension of a 0.1% aqueous solution: 40.6 dynes/cm (measured with a duNouy tensiometer).

An aqueous solution containing the remaining ingredients may be prepared by dissolving or dispersing the 5-fluorobenzonitrile or an acceptable salt thereof, preferably the hydrochloride, in amounts of from about 3% by weight to about 25% by weight and preferably 6 to 12% by weight of final formulation in deionized or distilled water used in amounts of from about 15% by weight to about 50% by weight and preferably 35 to 45% by weight of formulation. This solution is buffered by dissolving 1.5% by weight of citric acid and 1.0% by weight of trisodium citrate to provide a pH range at which long-term chemical stability of the components is achieved, i.e., pH 3–3.5.

Optional components, which may be incorporated into the above solution at this stage are:

a. Benzyl alcohol added in amounts of from about 0.5% by weight to about 1.5% by weight and preferably 1.5% by weight of formulation as an antimicrobial preservative;

b. The yellow dye C.I. Acid yellow No. 23, ("tartrazine," F.D. & C yellow No. 5; 4,5-dihydro-5-oxo-1-(4-sulfophenyl)-4-[(sulfophenyl)azo]-1H-pyrazole-3-carboxylic acid trisodium salt) used as a coloring agent in amounts of from about 0.01% by weight to about 0.03% by weight and preferably 0.01% by weight of formulation;

c. An antifoaming agent comprising a mixture of dimethylpolysiloxanes of structure:

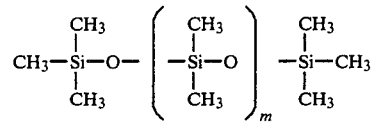

and silica gel, wherein the calculated average value of m is 200 to 350, the mixture is a water-white viscous oil-like liquid; d=0.965–0.970; $n_D{}^{25}$ about 1.404; viscosity about 60,000 centistrokes (and said-antifoaming agent is described in U.S. Pat. No. 2,441,098) used in amount of from 0.001 to 0.02% by weight and preferably 0.02% by weight of formulation.

The lipolytic and antilipogenic gel of this invention is prepared by simply mixing either of the above gellant phases and the aqueous solution from one-half hour to two hours under reduced pressure of from 10 to 100 mm Hg and preferably 25 to 50 mm Hg at ambient temperatures of from 20° to 60° C., without the requirements of either additional heating or cooling. This procedure gives an air-free gel which is suitable for administering exact dosages of the antilipogenic composition by volume.

Pellets for subcutaneous injection can be prepared by mixing a formula I, 5-fluorobenzonitrile or a pharmacologically acceptable salt thereof with a suitable diluent, such as montan wax, carbowax, carnauba wax or the like, and compressing the same into a pellet form. A lubricant such as magnesium or calcium stearate can be added to improve the pelleting process if so desired.

In order to obtain the drug dosage levels necessary to achieve desired results (i.e., increase in growth rates and/or improvement in lean meat to fat ratios), it may be necessary to administer multiple pellets. Also, implants may be made periodically during treatment periods in order to maintain proper drug levels in the animals.

In addition to improved growth rates and enhanced lean meat to fat ratios obtained with the compounds of this invention, administration of formula I compounds to meat-producing animals frequently results in enhanced efficiency of feed utilization thereby and reduced feed costs to bring the animals to market weight. With the use of materials and methods revealed in the present invention, producers can market superior quality meat animals in a short period of time while incurring minimum feed costs.

In view of the low $\beta_1$ activity, the compounds of the present invention, especially 3-[2-tert-butylamino)-1-hydroxyethyl]-5-fluorobenzonitrile, are useful for achieving bronchodilation in warm-blooded animals.

The following non-limiting examples further serve to illustrate the invention.

EXAMPLE 1

3-[2-(tert-Butylamino)-1-hydroxyethyl]-5-fluorobenzonitrile

In 2 L of CH$_2$Cl$_2$, 2-amino-5-fluoroacetophenone is stirred under N$_2$ and at 20° C.–25° C. 178 g of N- bromosuccinimide is added over 40 minutes. The mixture is stirred with 1.5 L of $H_2O$, and the $CH_2Cl_2$ solution is separated, washed further with $3 \times 1.5$ L of $H_2O$, dried over $Na_2SO_4$, filtered and evaporated to dryness in vacuo. The residue is washed with 200 mL of $CH_2Cl_2$, filtered, and the filter cake is washed with 200 mL of $CH_2Cl_2$ and dried to afford 637 g of 2-amino-3-bromo-5-fluoroacetophenone. Additional product (203 g) is obtained by stripping the mother liquors and washing the residue with MeOH. The combined crops melt at 75° C.–77° C. This material (210 g) is then added to 835 mL of $H_3PO_2$ and 835 mL of HOAc at 15° C. and 79.5 g of $NaNO_2$ is added in portions over a period of one hour and 10 minutes with vigorous stirring. After the reaction is completed, 2 L of $CH_2Cl_2$ is added and, after stirring, the $CH_2Cl_2$ solution is separated. The aqueous portion is further extracted with 100 mL of $CH_2Cl_2$. The organic extracts are washed with $2 \times 1$ L of $H_2O$, $2 \times 500$ mL of 5% NaOH solution and $2 \times 1$ L of $H_2O$ and dried over $Na_2SO_4$. The solution is filtered and evaporated to dryness to afford a tan solid, which is triturated with hexane and filtered to give 126.4 g, m.p. 75° C.–76° C., of 3-bromo-5-fluoroacetophenone. This material (217 g) is then stirred and heated at reflux temperature in 1490 mL of dimethylformamide containing 230.6 g of CuCN for six hours. After stirring at ambient temperature for 17 hours, the mixture is warmed to 80° C. and 792 g of $FeCl_3$ in 198 mL of concentrated HCl and 1188 mL of $H_2O$ is added. This is stirred at 60° C.–70° C. for 20 minutes, cooled to 30° C. and extracted with $CH_2CL_2$ ($3 \times 1$ L and $10 \times 0.5$ L). The combined $CH_2Cl_2$ solution is concentrated to about 2 L and, after 1 L of $CH_2Cl_2$ is added, the solution is washed with 1 L of $H_2O$ and 10% NaOH solution ($2 \times 500$ mL). The solution is filtered, further washed with $H_2O$ ($2 \times 750$ mL) and evaporated to dryness in vacuo to give 230.3 g of oily semisolid, which is distilled at 10° C.–100° C. to afford 180 g of solid distillate. The distillate is recrystallized from MeOH to yield 162 g of 3-cyano-5-fluoroacetophenone, m.p. 70° C.–70.5° C.

A solution containing 3-cyano-5-fluoroacetophenone in 1.8 L of $CH_2Cl_2$ with 10 drops of 30% HBr in HOAc is stirred at reflux temperature while 181.6 g of $Br_2$ is added slowly over a two-hour period. After five minutes of $Br_2$ addition, an additional 1 mL of 30% HBr in HOAc is added. The reaction mixture is stirred for 40 minutes after completion of $Br_2$ addition, cooled to room temperature, washed successively with 1.5 L of $H_2O$, $2 \times 1.2$ L of saturated $NaHCO_3$ solution and 1.5 L of $H_2O$, dried over $Na_2SO_4$, filtered and evaporated to dryness to afford 250 g of pale-yellow sticky solid, which is 3-cyano-5-fluorophenacyl bromide. This material (249 g) is stirred in 7.2 L of MeOH at 5° C. under $N_2$ and 29.7 g of $NaBH_4$ is added portionwise at 5° C.–8° C. After 25 minutes past the $NaBH_4$ addition, ice and 2 L of $H_2O$ are added, and the mixture is made acidic with 300 mL of 10% HCl to pH 2. The mixture is evaporated in vacuo to remove MeOH, and the turbid aqueous mixture is extracted with 2 L of $CH_2Cl_2$. The $CH_2Cl_2$ solution is washed with $2 \times 1.5$ L of $H_2O$, dried over $Na_2SO_4$, filtered and evaporated to dryness to afford 228.2 g of the corresponding bromohydrin. This crude material (227 g) is then reacted with excess t-$BuNH_2$ (1,531 g) in 2.2 L of EtOH under $N_2$ at reflux temperature for one and one-quarter hours. The mixture is evaporated in vacuo to remove excess t-$BuNH_2$ and EtOH to afford a red solid. This material is split into four portions and to each is added 200 mL of $H_2O$, ice, 500 mL of 10% NaOH and 1 L of $CH_2Cl_2$. The $CH_2Cl_2$ solution is separated after shaking, and the aqueous layer is further extracted with $2 \times 250$ mL of $CH_2Cl_2$. The $CH_2Cl_2$ solutions are combined, washed with 1 L of $H_2O$ and concentrated to 2 L (for the combined four portions). The $CH_2Cl_2$ solution is then extracted with HCl ($4 \times$ with 80 mL concentrated HCl in 1 L of $H_2O$). The aqueous acidic solution is extracted with 1 L of $CH_2Cl_2$ to remove some colored material, basified with 10% NaOH solution and extracted with $4 \times 1$ L of $CH_2Cl_2$. The combined extracts are washed with 1 L of $H_2O$, dried over $Na_2SO_4$, and evaporated to dryness in vacuo to afford 163.5 g of orange solid (A). To a 90 g portion of this solid A, 1 L of $CH_2Cl_2$, 0.6 L of $H_2O$, ice, and 180 mL of 10% HCl is added. The aqueous portion at pH<1 is adjusted to pH 5 with 10% NaOH and separated. The $CH_2Cl_2$ layer is washed with 400 mL of $H_2O$, and the $H_2O$ extract is added to the previous aqueous solution. The combined aqueous solution is washed with 400 mL of $CH_2Cl_2$, basified with 90 mL of 10% NaOH to pH>11 and extracted with $CH_2Cl_2$ ($2 \times 1$ L). The $CH_2Cl_2$ extracts are dried over $Na_2SO_4$, filtered, concentrated to 500 mL in vacuo, diluted with 400 mL of hexane and concentrated further to about 250 mL to afford a white solid, which is collected and washed with hexane to give 69.4 g of product, m.p. 96° C.–97° C. The remaining 73.5 g of A is worked up similarly to give 61.8 g, m.p. 96° C.–97° C. The two crops are combined to afford 3-[2-(tert-butylamino)-1-hydroxyethyl]-5-fluorobenzonitrile, m.p. 95° C.–96.5° C. with softening at 90° C.

EXAMPLE 2

Preparation of 3-fluoro-5-[1-hydroxy-2-(isopropylamino)ethyl]-benzonitrile

In the manner described in Example 1, 3-cyano-5-fluoroacetophenone is brominated and converted to the corresponding bromohydrin, which is allowed to react with excess isopropylamine to afford the title compound, m.p. 85.5° C.–86.5° C.

EXAMPLE 3

In the manner described in Example 1, the following products 2 are obtained by reacting the bromohydrin 1 with appropriate amines:

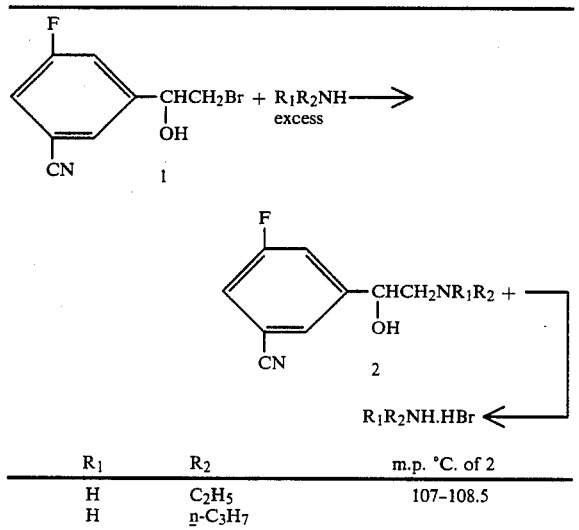

-continued

| | | |
|---|---|---|
| i-C$_3$H$_7$ | i-C$_3$H$_7$ | Yellow oil |
| H | 2-C$_5$H$_{11}$ | 65–66 |
| H | 2-C$_4$H$_9$ | |
| H | cyclobutyl | 109–110 |
| H | cyclopropyl | |
| H | cyclopentyl | |
| C$_2$H$_5$ | C$_2$H$_5$ | |
| CH$_3$ | n-C$_3$H$_7$ | |

EXAMPLE 4

Evaluation of test compounds as antilipogenic agents—mouse tests

CFI female mice from Carworth Farms are received when they are six-weeks old. They are housed ten to a cage in air-conditioned rooms (22° C. to 25° C.) with automatically-controlled lights, 14 hours on and ten hours off. The basal diet used in these studies is Purina Laboratory Chow (see description below) which is supplied ad libitum.

The following is a description of the diet to which the growth-promoting compounds were added.

| DIET Guaranteed Analysis | |
|---|---|
| Crude protein not less than | 23.0% |
| Crude fat not less than | 4.5% |
| Crude fiber not more than | 6.0% |
| Ash not more than | 9.0% |

Ingredients

Meat and bone meal, dried skimmed milk, wheat germ meal, fish meal, animal liver meal, dried beet pulp, ground extruded corn, ground oat groats, soybean meal, dehydrated alfalfa metal, cane molasses, animal fat preserved with BHA, vitamin B$_{12}$ supplement, calcium pantothenate, choline chloride, folic acid, riboflavin supplement, brewer's dried yeast, thiamin, niacin, vitamin A supplement, D-activated plant sterol, vitamin E supplement, calcium carbonate, dicalcium phosphate, iodized salt, ferric ammonium citrate, iron oxide, manganous oxide, cobalt carbonate, copper oxide, zinc oxide. Water is also allowed ad libitum.

Thirteen days after arrival, the mice are weighed in groups of ten and assigned at random to the different treatments. Each of the treatments is tested in three replicates, i.e., in three cages of ten mice each. There are ten cages of ten control mice each. Drugs are mixed in the diet at the dosage level indicated. Feed and water are offered ad libitum for a 12-day test period. Feed spilled is collected during the test period. At the end of the test period, the collected feed is weighed, and the mean feed consumption per cage of ten mice is determined for each treatment. The mice are weighed as a group of ten, and the weight gain determined. The mice are sacrificed by cervical dislocation. The right uterine fat pad of each mouse is removed. The fat pads for each cage of ten mice are weighed as a unit. Reduction in fat pad weights of animals is generally indicative of a reduction of total body fat of the treated animals.

Moreover, when a significant decrease in body fat is coupled with a marked improvement in weight gain in the treated animals, we have found that the lean meat to fat ratio of said-treated animals is substantially improved.

Data obtained are reported in Table I below.

TABLE I

ANTILIPOGENIC EVALUATION OF TEST COMPOUNDS-MOUSE STUDY

| Compound | Dosage (ppm) | % Reduction in Fat Pad Weight vs Controls | % Change in Body Weight vs controls |
|---|---|---|---|
| 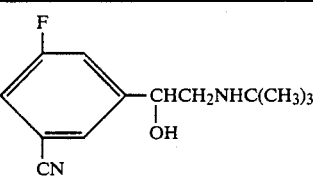 | 200 | −38.13 | +55.93 |
| | 100 | −29.65 | +65.25 |
| | 50 | −14.04 | +80.51 |
| | 25 | −8.97 | +96.61 |
| 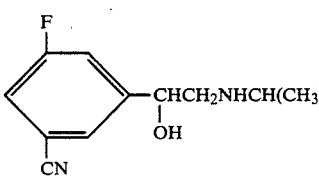 | 200 | −33.29 | +88.32 |
| | 100 | −17.71 | +56.93 |
| | 50 | +9.90 | +78.10 |
| | 25 | +9.76 | +29.20 |
| | 12.5 | −11.76 | +26.28 |
| | 6 | +5.91 | +40.88 |
| | 3 | +0.93 | +0.73 |
| 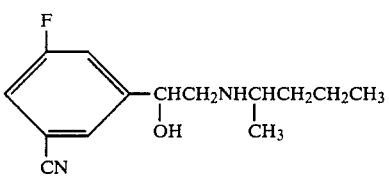 | 200 | −22.8 | +22.4 |
| | 100 | −15.5 | +1.2 |
| | 50 | −5.6 | +15.9 |

TABLE I-continued

ANTILIPOGENIC EVALUATION OF TEST COMPOUNDS-MOUSE STUDY

| Compound | Dosage (ppm) | % Reduction in Fat Pad Weight vs Controls | % Change in Body Weight vs controls |
|---|---|---|---|
| 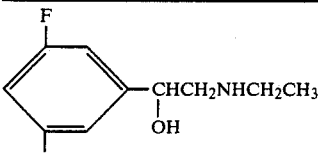 | 200 | −37.9 | +25.3 |
| | 100 | −33.3 | −4.1 |
| | 50 | +4.3 | +18.8 |
| 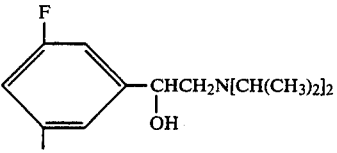 | 200 | −19.36 | +19.05 |
| | 50 | −15.39 | −2.38 |

EXAMPLE 5

Determination of beta-1 adrenergic activity of experimental repartitioning compounds Beta-1 adrenergic activity of experimental compounds is identified by radioactive ligand-binding studies by using beta adrenergic receptor membranes and adrenergic antagonist (H3) dihydroalprenolol (DHA). Binding of (H3) DHA to membrane fractions is assayed by filtration on glass fiber filters. Specific binding is defined as total radioactivity bound minus nonspecific bound radioactivity, i.e., binding in the presence of 100 $\mu$M nonradioactive DHA. Results are expressed as the concentrations of the compound required to displace 50% radioactive ligand from binding of beta adrenergic receptors (K-50).

In these tests, beta adrenergic receptor membranes are incubated with radioactive dihydroalprenolol (H3 DHA) and experimental compounds. The bound radio-ligand is separated by filtration on glass fiber filters and counted by scintillation counter.

Radioactive ligand, H3 dihydroalprenolol (DHA) and aquasol are purchased from New England Nuclear Corporation, DMSO is supplied by J. T. Baker Company, and all other chemicals are obtained from Sigma Chemical Company.

Beta-1 adrenergic receptor membranes are isolated from turkey and rat erythrocytes respectively using the procedures of:

Hancock, A., DeLean, A., Lefkowitz, R. J. Mol. Pharmacol. 16:1, 1979;

DeLean, A, Hancock A., Lefkowitz, R. J. Mol. Pharmacol. 21:5, 1979; or,

Lefkowitz, R. J., Stadel, J. M., and Caron, M. G. Ann. Rev. Biochem 52:157, 1983.

Freshly drawn heparinized whole blood from turkeys and rats is centrifuged for five minutes (4×500 g). The plasma is withdrawn; the remaining erythrocytes are suspended in 150 mM sodium chloride solutions and centrifuged. The cells are resuspended and centrifuged twice more. The cells are hemolyzed in 10 volume of cold distilled water containing 2 mM dithiothreitol, 100 $\mu$M phenylmethyl sulfonyl fluoride, 5 $\mu$g/mL leupeptin, 200 $\mu$g/mL bacitacin, 0.1% bovine serum albumin, and 10 units/mL aprotonin, and centrifuged at 3000×g for five minutes. The bottom gelatin layer is discarded. The top layer is suspended and centrifuged five times at 3000×g and resuspended in tris buffer (145 mM NaCl, 1 mM ethylene glycol-bis($\beta$-aminoethyl ether) N,N,N,N, tetraacetic acid, 2 mM MgCl$_2$, 10 mM tris, and 10% glycerol, pH 7.4). The resuspended membranes are further purified with differential centrifugation by using sucrose albumin cushion, and subsequently stored in small aliquots at −70° C. The protein concentration of receptor membranes is determined by the biuret method.

To duplicate incubation, tubes are added 200 $\mu$l suspended membranes (200 $\mu$g protein), 25 $\mu$l of compound in solution or buffer and 25 $\mu$l (H3) dihydroalprenolol (200,000 CPM). Tubes were incubated at room temperature (23° C.) for an hour and then filtered rapidly under vacuum through Whatman GF/B filters. The filters are rinsed three times with 5 mL of cold buffer (145 mM NaCl, 1 mM ethylenediaminetetraacetic acid, and 10 mM tris, pH 7.4) and subsequently counted by liquid scintillation counter in 10 mL of aquasol. Specific binding of H3 DHA is defined as the excess over blank containing 100 $\mu$M nonradioactive DHA. Six serial dilutions of each compound are tested.

Beta adrenergic activity is inversely related to K-50 (the concentrations of the compound required to displace 50% radioactive ligand from binding sites of beta adrenergic receptors, i.e., 50% binding) value.

Data obtained are reported in Table II below.

TABLE II

BETA-1 ADRENERGIC ACTIVITY DETERMINED AS K-50 (THE CONCENTRATIONS OF THE COMPOUND REQUIRED TO DISPLACE 50% RADIOACTIVE LIGAND FROM BINDING SITES OF BETA ADRENERGIC RECEPTORS, i.e., 50% BINDING) VALUE FOR 5-FLUORO-BENZONITRILE DERIVATIVES WITH CLENBUTERAL AS A STANDARD

| Compound | $\beta_1$ K-50 ($\mu$M) |
|---|---|
| 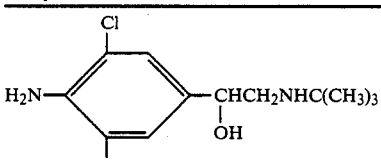 | 0.977 |

*Clenbuterol (Standard)

TABLE II-continued

BETA-1 ADRENERGIC ACTIVITY DETERMINED AS K-50 (THE CONCENTRATIONS OF THE COMPOUND REQUIRED TO DISPLACE 50% RADIOACTIVE LIGAND FROM BINDING SITES OF BETA ADRENERGIC RECEPTORS, i.e., 50% BINDING) VALUE FOR 5-FLUOROBENZONITRILE DERIVATIVES WITH CLENBUTERAL AS A STANDARD

| Compound | $\beta_1$ K-50 ($\mu$M) |
|---|---|
| F—C$_6$H$_3$(CN)—CH(OH)CH$_2$NHCH(CH$_3$)CH$_2$CH$_3$ | 2.197 |
| F—C$_6$H$_3$(CN)—CH(OH)CH$_2$N[CH(CH$_3$)$_2$]$_2$ | 2.948 |
| F—C$_6$H$_3$(CN)—CH(OH)CH$_2$NHCH$_2$CH$_3$ | 3.041 |
| F—C$_6$H$_3$(CN)—CH(OH)CH$_2$NHCH(CH$_3$)$_2$ | 12.260 |
| F—C$_6$H$_3$(CN)—CH(OH)CH$_2$NHC(CH$_3$)$_3$ | 16.644 |

*Clenbuterol is a very effective bronchodilator and a potent heart stimulant. It is used in this evaluation for comparison. The lower the numerical value reported for the $\beta_1$, K-50 ($\mu$M) value, the more active the compound is as a heart stimulant.

EXAMPLE 6

Antilipogenic evaluation of test compounds—mouse study

Following the procedure of Example 4, the analogues of the compounds of the invention in the subject Application are evaluated as antilipogenic agents.

Data obtained are reported in Table III below where it can be seen that 3-[2-(tert-butylamino)-1-hydroxyethyl]-5-fluorobenzonitrile is markedly more effective as an antilipogenic agent than its related aanalogues. It can also be seen that 3-fluoro-5-[1-hydroxy-2-(isopropylamino)ethyl]benzonitrile, when administered at 100 ppm or 200 ppm in the diet, is also generally more effective as an antilipogenic agent than its related analogues administered at similar rates.

TABLE III

ANTILIPOGENIC EVALUATION OF TEST COMPOUNDS - MOUSE STUDY

| Compound | Dose PPM | Mouse Test Fat Pad Weight % ± Control |
|---|---|---|
| F—C$_6$H$_3$(CN)—CH(OH)CH$_2$NHC(CH$_3$)$_3$ | 200 | −42.9 |
| | 100 | −38.4 |
| F—C$_6$H$_3$(CN)—CH(OH)CH$_2$NHCH(CH$_3$)$_2$ | 200 | −33.3 |
| | 100 | −17.7 |

EXAMPLE 7

Evaluation of 3-[2-(tert-butylamino)-1-hydroxyethyl]-5-fluorobenzonitrile as an animal feed additive for (1) the enhancement of the growth rate of poultry, (2) improvement in feed utilization thereby, (3) increase in the deposition of muscle tissue or protein in said birds and (4) improvement in the carcass quality of treated birds One-day old Hubbard X Hubbard Crossbred Chicks, randomly allotted to pens of ten chicks (five males and five females) each.

Eight pens of chicks are used for unmedicated controls, and six pens of chicks are used at each level of drug. The duration of the experiment is seven weeks.

The controls are offered an unmedicated diet of Broiler Ration No. 453 (composition given below) and water ad libitum. Medicated chicks are offered the same diet containing the test drug at the levels indicated above, and water ad libitum. The weight of the chicks is determined at the beginning and on completion of the experiments. Weight gains and the amount of feed consumed are also determined. In addition, ten males and ten females from each group are randomly selected and sacrificed by decapitation. These birds were bled, the feathers, feet, and viscera removed, and the resulting carcass weighed. The results of these tests are reported in Table IV below where it can be seen that chicks receiving from 0.25 ppm to 2.0 ppm of the test compound showed an increase in growth rate, improvement in utilization of their feed, and increased carcass yield.

The thus-obtained data are averaged and summarized in Table IV below, wherein the percent improvement in weight gains and feed/gain ratios are given.

| Component | Percent by Weight |
|---|---|
| Ground yellow corn | 53.45 |
| Soybean oil meal (49%) | 28.00 |
| Menhaden fish meal (60%) | 5.00 |
| Corn gluten meal (60%) | 5.00 |
| Dehydrated alfalfa meal (17%) | 2.00 |
| Stabilized fat | 4.00 |
| Dicalcium phosphate | 1.20 |
| Ground limestone | 0.50 |
| Sodium chloride | 0.30 |
| Trace minerals mixture* | 0.05 |

| | |
|---|---|
| Vitamin premix** | 0.50 |
| | 100.00 |

| *Trace Mineral Mixture | 454 g/ton Furnishes |
|---|---|
| Manganese | 62.5 ppm |
| Iron | 30.0 |
| Zinc | 25.0 |
| Copper | 3.25 |
| Iodine | 1.75 |
| Cobalt | 1.25 |

| **Vitamin Premix for One-Ton | Weight in Grams |
|---|---|
| DL Methionine | 453.6 |
| BHT (butylated hydroxy toluene) | 113.6 |
| Vitamin A (30,000 mcg/g) | 100.0 |
| Vitamin $D_3$ (200,000 mcg/g) | 5.0 |
| Vitamin E (20,000 mcg/lb) | 45.4 |
| Riboflavin | 4.0 |
| Niacinamide | 25.0 |

TABLE IV
EVALUATION OF 3-[2-TERT-BUTYLAMINO)-1-HYDROXYETHYL]-5-FLUOROBENZONITRILE FOR INCREASING THE GROWTH RATE OF POULTRY, IMPROVING EFFICIENCY OF FEED UTILIZATION THEREBY AND INCREASING THE CARCASS YIELD OF SAID POULTRY (BROILERS)

| | PPM IN DIET | | | | |
|---|---|---|---|---|---|
| | 0 | .25 | .5 | 1 | 2 |
| Gain (kg) | 1.078 | 1.105 | 1.132 | 1.097 | 1.114 |
| Percent (±) Control | | +2.5 | +5.0 | +1.9 | +3.3 |
| Feed Consumed (kg) | 2.567 | 2.576 | 2.571 | 2.573 | 2.578 |
| Percent (±) Control | | +0.4 | +0.2 | +0.2 | +0.4 |
| *FE | 2.384 | 2.333 | 2.274 | 2.350 | 2.315 |
| Percent (±) Control | | +2.1 | +4.6 | +1.4 | +3.0 |
| Carcass Yield (Percent of live weight) | 68.74 | 69.46 | 68.73 | 69.66 | 69.30 |
| Percent (±) Control | | +1.0 | 0.0 | +1.3 | +0.8 |

*FE = Feed efficiency

EXAMPLE 8
Evaluation of 3-[2-(tert-butylamino)1-hydroxyethyl]-5-fluorobenzonitrile for growth enhancement, feed efficiency improvement, increased deposition of muscle tissue and/or protein and improvement in carcass composition To determine the effect of feeding experimental compounds to ruminants, wether lambs are randomly allotted to pens in groups of five. Three replications per treatment are used. The lambs are weighed and permitted feed and water ad libitum. The feed is weighed daily, and uneaten feed from the previous day is collected and weighed. Test lambs receive the same diet as control animals, but with the addition of experimental compound at a concentration of from 5 ppm to 20 ppm. The tests are conducted for a period of eight weeks at the end of which the lambs are again weighed, and the feed consumed calculated. The lambs are then necropsied. Eight animals per treatment are dressed, and the average cross-sectional area of the longissimus dorsi and depth of subcutaneous fat measured at the 12th rib.

Data obtained are reported in Table V below.

TABLE V
EVALUATION OF 3-[2-(TERT-BUTYLAMINO)-1-HYDROXYETHYL]-5-FLUOROBENZONITRILE FOR INCREASING THE GROWTH RATE OF RUMINANTS, IMPROVING FEED EFFICIENCY, ENHANCING THE DEPOSITION OF MUSCLE TISSUE AND REDUCING THE DEPOSITION OF ADIPOSE TISSUE IN LAMBS

| | PPM IN DIET | | | |
|---|---|---|---|---|
| | 0 | 5 | 10 | 20 |
| *ADG (g) | 203 | 226 | 253 | 234 |
| Percent (±) Control | | +11.3 | +24.6 | +15.3 |
| *AD Feed Consumed (kg/day) | 1.39 | 1.43 | 1.50 | 1.39 |
| Percent (±) Control | | +2.9 | +7.9 | +0.0 |
| ***FE | 6.84 | 6.36 | 5.91 | 5.92 |
| Percent (±) Control | | +7.0 | +13.6 | +13.5 |
| Carcass Yield (Percent of live weight) | 50.86 | 51.80 | 51.52 | 54.15 |
| Percent (±) Control | | +1.8 | +1.3 | +6.5 |
| Muscle Cross-Sectional Area ($cm^2$) | 16.56 | 17.69 | 18.44 | 20.56 |
| Percent (±) Control | | +6.8 | +11.4 | +24.2 |
| Subcutaneous Fat Depth Over Loin (cm) | 4.2 | 3.2 | 2.7 | 1.8 |
| Percent (±) Control | | +23.8 | +35.7 | +57.1 |

*ADG = Average daily gain.
**AD Feed Consumed = Average daily feed consumed.
***FE = Feed efficiency.

What is claimed is:

1. A compound of the formula:

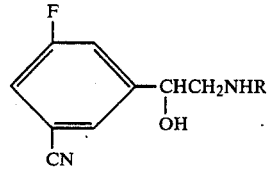

wherein R is isopropyl or tert-butyl; or an optical isomer thereof or a non-toxic pharmacologically acceptable acid addition salt of the above-said compound.

2. A compound according to claim 1, 3-[2-tert-butylamino)-1-hydroxyethyl]-5-fluorobenzonitrile.

3. A compound according to claim 1, 3-fluoro-5-[1-hydroxy-2-(isopropylamino)ethyl]benzonitrile.

4. A method for increasing the lean meat to fat ratio, and/or improving the efficiency of feed utilization, and/or enhancing the growth rate of warm-blooded animals comprising: orally or parenterally administering to said animals an effective amount to achieve at least one of the animal body functions above, of a compound of the formula:

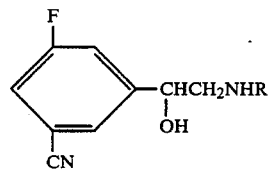

wherein R is isopropyl or tert-butyl; or an optical isomer thereof or a non-toxic pharmacologically acceptable acid addition salt of the above-said compound.

5. A method according to claim 4 for increasing the lean meat to fat ratio of warm-blooded animals wherein said animals are poultry, swine, sheep, or cattle.

6. A method according to claim 4 for improving feed efficiency in warm-blooded animals wherein said animals are poultry, swine, sheep, or cattle.

7. A method according to claim 4 for enhancing the growth rate of warm-blooded animals wherein said animals are poultry, swine, sheep, or cattle.

8. A method according to claim 4, wherein the compound is 3-[2-(tert-butylamino)-1-hydroxyethyl]-5-fluorobenzonitrile.

9. A method according to claim 4, wherein the compound is 3-fluoro-5-[1-hydroxy-2-(isopropylamino)ethyl]benzonitrile.

10. A method according to claim 4, wherein said warm-blooded animals are swine, poultry, sheep, goats, domestic pets or cattle, and the compound is orally administered to said animals in an animal feed containing from 0.05 to 200 grams of said compound per ton of feed.

11. A method according to claim 4, wherein said warm-blooded animals are swine, poultry, sheep, goats, domestic pets, or cattle, and the compound is parenterally administered to said animals by subcutaneous injection of an implant composition containing sufficient compound to provide said animals with from 0.001 to 100 mg/kg/day of body weight of said compound.

12. An animal feed composition comprising an edible animal feed containing from 0.05 to 200 grams per ton of feed of a compound of the formula:

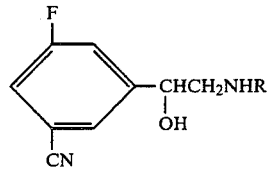

wherein R is isopropyl or tert-butyl; or an optical isomer thereof or a non-toxic pharmacologically acceptable acid addition salt of the above-said compound.

13. A composition according to claim 12, wherein the compound is 3-[2-(tert-butylamino)-1-hydroxyethyl]-5-fluorobenzonitrile.

* * * * *